(12) United States Patent
Suzushima et al.

(10) Patent No.: US 7,993,265 B2
(45) Date of Patent: Aug. 9, 2011

(54) IN-VIVO IMAGE ACQUIRING SYSTEM AND BODY-INSERTABLE APPARATUS

(75) Inventors: Hiroshi Suzushima, Nagano (JP); Noriyuki Fujimori, Suwa (JP); Tatsuya Orihara, Hachioji (JP); Masatoshi Homan, Hino (JP); Takemitsu Honda, Hino (JP); Kazutaka Nakatsuchi, Hino (JP)

(73) Assignee: Olympus Corporation, Tokyo (JP)

( * ) Notice: Subject to any disclaimer, the term of this patent is extended or adjusted under 35 U.S.C. 154(b) by 1211 days.

(21) Appl. No.: 11/658,552

(22) PCT Filed: Aug. 5, 2005

(86) PCT No.: PCT/JP2005/014443
§ 371 (c)(1),
(2), (4) Date: Jan. 25, 2007

(87) PCT Pub. No.: WO2006/013977
PCT Pub. Date: Feb. 9, 2006

(65) Prior Publication Data
US 2009/0012357 A1 Jan. 8, 2009

(30) Foreign Application Priority Data
Aug. 6, 2004 (JP) ................................ 2004-231113

(51) Int. Cl.
*A61B 1/04* (2006.01)
(52) U.S. Cl. ......... 600/170; 600/109; 600/117; 600/176
(58) Field of Classification Search .................. 600/160, 600/109, 103, 117, 170, 171, 176, 407, 476
See application file for complete search history.

(56) References Cited

U.S. PATENT DOCUMENTS

| | | | |
|---|---|---|---|
| 4,532,544 A * | 7/1985 | Federau | 348/37 |
| 5,604,531 A | 2/1997 | Iddan et al. | |
| 5,827,176 A | 10/1998 | Tanaka et al. | |
| 6,233,476 B1 * | 5/2001 | Strommer et al. | 600/424 |

(Continued)

FOREIGN PATENT DOCUMENTS

DE 34 40 177 A1 5/1986

(Continued)

OTHER PUBLICATIONS

English language abstract of Japanese Patent Application Publication No. JP2003-070728A, Dec. 26, 2002.

(Continued)

*Primary Examiner* — John P Leubecker
(74) *Attorney, Agent, or Firm* — Scully, Scott, Murphy & Presser, PC

(57) ABSTRACT

A capsule endoscope 2 includes a partial-image acquiring unit that has a field of vision of 360° around a central axis in a longitudinal direction (moving direction), and acquires a plurality of partial image data on inner circumferential areas 28a, 28b and the like according to a movement of the capsule endoscope 2. On the other hand, the capsule endoscope 2 is configured to acquire position related data based on which positions Z(t1) and Z(t2) at which the respective partial image data is acquired can be calculated, and enables a receiving apparatus or the like to constitute overall image data based on the partial image data and the position related data, whereby an overall image of a predetermined imaging target in a body of a subject is acquired with simple constitution while suppressing an increase in data amount.

25 Claims, 9 Drawing Sheets

U.S. PATENT DOCUMENTS

| | | | |
|---|---|---|---|
| 6,248,074 B1* | 6/2001 | Ohno et al. | 600/463 |
| 6,904,308 B2 | 6/2005 | Frisch et al. | |
| 6,939,292 B2* | 9/2005 | Mizuno | 600/118 |
| 7,336,833 B2* | 2/2008 | Horn | 382/232 |
| 7,625,335 B2* | 12/2009 | Deichmann et al. | 600/117 |
| 7,744,528 B2* | 6/2010 | Wallace et al. | 600/170 |
| 7,801,584 B2* | 9/2010 | Iddan et al. | 600/407 |
| 2002/0052547 A1* | 5/2002 | Toida | 600/425 |
| 2002/0109774 A1 | 8/2002 | Meron et al. | |
| 2002/0198439 A1 | 12/2002 | Mizuno | |
| 2003/0045790 A1 | 3/2003 | Lewkowicz et al. | |
| 2003/0167000 A1* | 9/2003 | Mullick et al. | 600/424 |
| 2003/0195415 A1* | 10/2003 | Iddan | 600/424 |
| 2003/0208107 A1 | 11/2003 | Refael | |
| 2004/0054278 A1 | 3/2004 | Kimchy et al. | |
| 2005/0025368 A1* | 2/2005 | Glukhovsky | 382/236 |
| 2005/0096526 A1 | 5/2005 | Reinschke | |
| 2006/0106283 A1* | 5/2006 | Wallace et al. | 600/109 |
| 2007/0060792 A1* | 3/2007 | Draxinger et al. | 600/117 |

FOREIGN PATENT DOCUMENTS

| | | |
|---|---|---|
| JP | 9-215660 | 8/1997 |
| JP | 2003-70728 A | 12/2002 |
| JP | 2003-19111 A | 1/2003 |
| JP | 2004-154176 | 6/2004 |
| JP | 2005-111273 | 8/2005 |

OTHER PUBLICATIONS

Extended Supplementary Partial European Search Report dated Sep. 14, 2009.

* cited by examiner

46 PARTIAL IMAGE DATA

IN-VIVO IMAGE ACQUIRING SYSTEM AND BODY-INSERTABLE APPARATUS

TECHNICAL FIELD

The present invention relates to an in-vivo image acquiring system for acquiring an image of an imaging target in a body of a subject, and a body-insertable apparatus used when an image of an imaging target in a body of a subject is to be acquired.

BACKGROUND ART

In recent years, a swallowable capsule endoscope has been proposed in the field of endoscopes. The capsule endoscope includes an imaging mechanism and a radio communication mechanism. The capsule endoscope functions to move in body cavities such as interiors of organs, e.g., the stomach and the small intestine, according to peristaltic movements of the organs, and to pick up intra-subject images at intervals of, for example, 0.5 second until natural discharge of the capsule endoscope after a subject (human body) swallows the capsule endoscope from his/her mouth for observation (examination).

During the movement of the capsule endoscope in the body cavities, image data on images picked up by the capsule endoscope is sequentially transmitted to an outside by radio communication, and accumulated in a memory provided outside. By carrying a receiving apparatus including a radio communication function and a memory function, the subject can act freely since swallowing the capsule endoscope until discharging it. After the capsule endoscope is discharged, a doctor or a nurse can diagnose the subject while displaying the images of the organs based on the image data accumulated in the memory on a display (see, for example, Patent Document 1).

Patent Document 1: Japanese Patent Application Laid-Open No. 2003-19111

DISCLOSURE OF INVENTION

Problem to be Solved by the Invention

However, the conventional capsule endoscope system has a problem that it is difficult to pick up an overall image of an area such as the esophagus in which the capsule endoscope moves at high velocity. If the subject maintains, for example, an upright state, then the esophagus connects an oral cavity to the stomach while the esophagus extends in vertical direction, and the capsule endoscope inserted into the body of the subject reaches the stomach in a similar state to a state of free fall after passing through the oral cavity. Considering that an entire length of the esophagus is about 30 centimeters, the capsule endoscope passes through the esophagus within about one second, so that the capsule endoscope can image only a small area of the esophagus by using an ordinary imaging mechanism at the imaging rate of about 0.5-second intervals, and it is quite difficult to acquire image data on the entire esophagus.

Due to this, it is necessary for the conventional capsule endoscope to include an imaging mechanism that has, for example, a wide imaging field of vision to acquire image data on, for example, the entire esophagus. To realize such a configuration, however, it is unfavorably necessary to provide a complicated optical system and the like, with the result that a problem of making the capsule endoscope large in size or the like, in turn, occurs.

Furthermore, the imaging rate can be accelerated to acquire the overall image data on the esophagus or the like. However, if the imaging rate is accelerated, then an amount of the acquired image data increases and an amount of transmitted data often increases depending on the radio mechanism. Accordingly, if the imaging rate is increased, new problems occur that the data amount to be processed increases and power consumption of the capsule endoscope increases. Such a configuration is, therefore, unfavorable.

The present invention has been achieved in view of the above-stated respects, and it is an object of the present invention to realize a body-insertable apparatus such as a capsule endoscope capable of acquiring an overall image of a predetermined imaging target in the body of a subject with simple configuration while suppressing an increase in data amount, and to realize an in-vivo image acquiring system using the body-insertable apparatus.

Means for Solving Problem

An in-vivo image acquiring system for acquiring an image of a predetermined imaging target in a body of a subject according to the present invention, includes a partial-image acquiring unit that acquires a plurality of partial image data corresponding to different parts of the imaging target in the body of the subject; a position-related-data acquiring unit that acquires position related data used to calculate a position of the partial-image acquiring unit in the body of the subject when the partial-image acquiring unit acquires each of the partial image data; and an overall-image generator that generates overall image data corresponding to an overall image of the imaging target using the plurality of partial image data based on the position related data.

According to the invention, the in-vivo image acquiring system includes the partial-image acquiring unit that acquires the partial image data and the position-related-data acquiring unit that acquires the position related data corresponding to each partial image, and includes the overall-image generator that acquires the overall image of the imaging target based on the partial image data and the position related data. It is, therefore, advantageously possible to reduce the number of pixels of an imaging mechanism that realizes the partial-image acquiring unit and construct the system with simple configuration.

In the in-vivo image acquiring system according to the invention, the partial-image acquiring unit and the position-related-data acquiring unit may be included in a body-insertable apparatus that transmits a predetermined radio signal and is inserted into an interior of the subject, and the overall-image generator may be included in a receiving apparatus that receives the radio signal transmitted from the body-insertable apparatus and is arranged outside the subject when in use.

In the in-vivo image acquiring system according to the invention, the body-insertable apparatus may further include a data synthesizer that generates overall-image generation data generated based on the partial image data and the position related data; and a transmitter that transmits the radio signal including the overall-image generation data generated by the data synthesizer, and wherein the receiving apparatus may further include a receiving circuit that performs a predetermined receiving processing on the radio signal transmitted by the transmitter and that outputs the extracted overall-image generation data to the overall-image generator.

In the in-vivo image acquiring system according to the invention, the partial-image acquiring unit may include a line sensor including a plurality of photoelectric conversion mechanisms arranged in the body of the subject in a direction perpendicular to a moving direction.

In the in-vivo image acquiring system according to the invention, the position-related data acquiring unit may include an acceleration sensor unit that acquires at least acceleration data on a movement of the partial-image acquiring unit as the position related data.

In the in-vivo image acquiring system according to the invention, the partial-image acquiring unit may change an interval of acquiring the partial image data according to a moving velocity of the body-insertable apparatus.

In the in-vivo image acquiring system according to the invention, driving of the partial-image acquiring unit may be stopped in a period in which a moving direction of the body-insertable apparatus becomes opposite.

Furthermore, a body-insertable apparatus insertable and movable in a body of the subject according to the present invention, includes a partial-image acquiring unit that acquires a plurality of partial image data corresponding to different parts of an imaging target in the body of the subject according to a movement of the body-insertable apparatus in the body of the subject; a position-related-data acquiring unit that acquires position related data necessary to calculate a position of the partial-image acquiring unit in the body of the subject when the partial-image acquiring unit picks up each of the partial image data; a data synthesizer that generates overall-image generation data used to generate overall image data corresponding to an overall image of the imaging target, based on the partial image data and the position related data; and a transmitter that transmits a radio signal including the overall-image generation data.

Effect of the Invention

Each of the in-vivo image acquiring system and the body-insertable apparatus according to the present invention includes the partial-image acquiring unit that acquires the partial image data and the position-related-data acquiring unit that acquires the position related data corresponding to each partial image. It is, therefore, advantageously possible to generate the overall image data on the imaging target based on the partial image data and the position related data, reduce the number of pixels of an imaging mechanism that realizes the partial-image data acquiring unit, and construct the system with simple configuration.

EXPLANATIONS OF LETTERS OR NUMERALS

Figure 1:
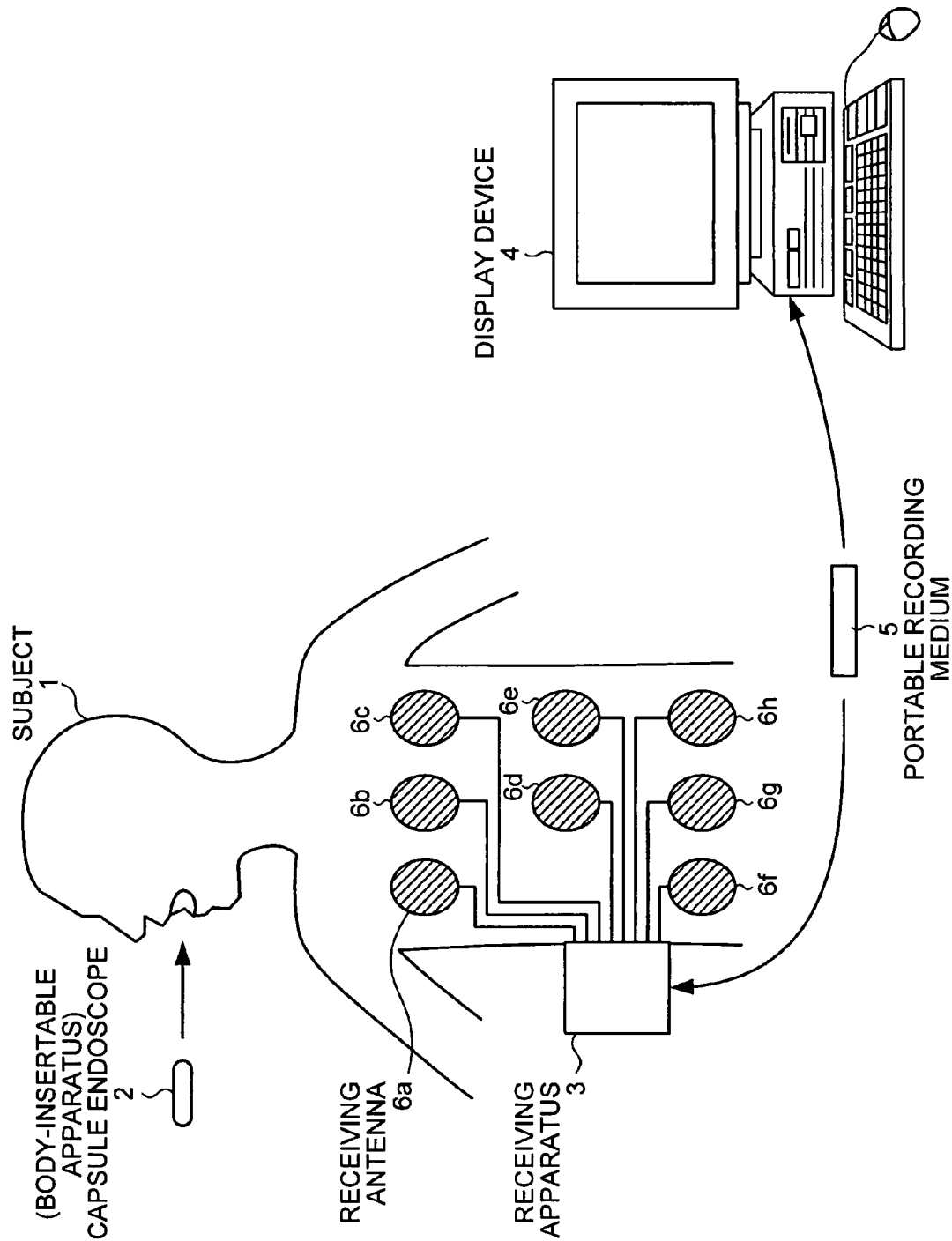
FIG. 1 is a pattern diagram showing an overall configuration of an in-vivo image acquiring system according to an embodiment.

1 Subject
2 Capsule endoscope
3 Receiving apparatus
4 Display device
5 Portable recording medium
6a-6h Receiving antenna
8 Partial-image acquiring unit
9 Acceleration sensor unit
10 Data synthesizer
11 Transmitting unit
12 Control unit
13 Power supply unit
14, 14a, 14b Line sensor unit
15 Sensor driving circuit
16, 16a, 16b LED
17 LED driving circuit
18 Transmitting circuit
19 Transmitting antenna
21 External case member
21a Imaging window
22a, 22b Prism
24a, 24b Incidence mirror
25a-25d Light-guiding mirror
27 Esophagus
28a, 28b Inner circumferential area
30a, 30b Overall-image generation data
31 Partial image data
32 Position related data
32a Time data
32b Acceleration data
33 Position related data
33a Time data
33b Acceleration data
35 Antenna selector
36 Receiving circuit
37 Signal processor
38 Data separator
39 Position data generator
40 Overall-image generator
41 Control unit
42 A/D converter
43 Storage unit
44 Power supply unit
46 Partial image data
47 Overall image data

BEST MODE(S) FOR CARRYING OUT THE INVENTION

A body-insertable apparatus and an in-vivo image acquiring system as best modes for carrying out the invention (hereinafter, simply "embodiments") will be described hereinafter. It is to be noted that the drawings are pattern diagrams and that the relation between a thickness and a width of each element, a thickness rate of each element, and the like differ from actual ones, and it goes without saying that elements different in dimensional relation and rate among the drawings are included in the drawings.

FIG. 1 is a pattern diagram showing an overall configuration of an in-vivo image acquiring system according to an embodiment of the present invention. As shown in FIG. 1, the in-vivo image acquiring system according to the embodiment includes a capsule endoscope 2 inserted into the body of a subject 1 and moving along a passing route, a receiving apparatus 3 that receives a radio signal transmitted from the capsule endoscope 2 and including overall-image generation data (to be described later), and that generates overall image data on an overall image of an imaging target based on the overall-image generation data, a display device 4 that displays the overall image data or the like generated by the receiving apparatus 3, and a portable recording medium 5 that mediates between the receiving apparatus 3 and the display device 4 for transmitting and receiving data therebetween.

The display device 4 is to display the overall image data that is data on the overall image of the imaging target, and is configured, like a workstation or the like, to display images based on data input through the portable recording medium 5. Specifically, the display device 4 can be configured to directly display images and the like by a CRT display, a liquid crystal display or the like, or configured, like a printer or the like, to output images and the like to the other medium.

The portable recording medium 5 is detachable from the receiving apparatus 3 and the display device 4, and is structured to be able to output and record data when being attached to the both. Specifically, the portable recording medium 5 is configured so that, when the capsule endoscope 2 is moving in the body cavities of the subject 1, the portable recording medium 5 is attached to the receiving apparatus 3 and stores therein in-vivo images. After the capsule endoscope 4 is discharged from the subject 1, the portable recording medium 5 is detached from the receiving apparatus 3 and attached to the display device 4, and recorded data is read by the display device 4. By causing the portable recording medium 5 such as a compact flash (registered trademark) memory to mediate between the recording apparatus 3 and the display device 4 for transmitting and receiving data therebetween, the subject 1 can act freely even while the capsule endoscope 2 is moving in the body of the subject 1, differently from an instance in which the receiving apparatus 3 and the display device 4 are wired-connected.

Each of the receiving antennas 6a to 6h is formed using, for example, a loop antenna. The respective loop antennas are configured to be fixed to predetermined positions on a body surface of the subject 1, and to be electrically connected to the receiving apparatus 3, whereby the receiving apparatus 3 can receive a radio signal transmitted from the capsule endoscope 2.

Figure 2:
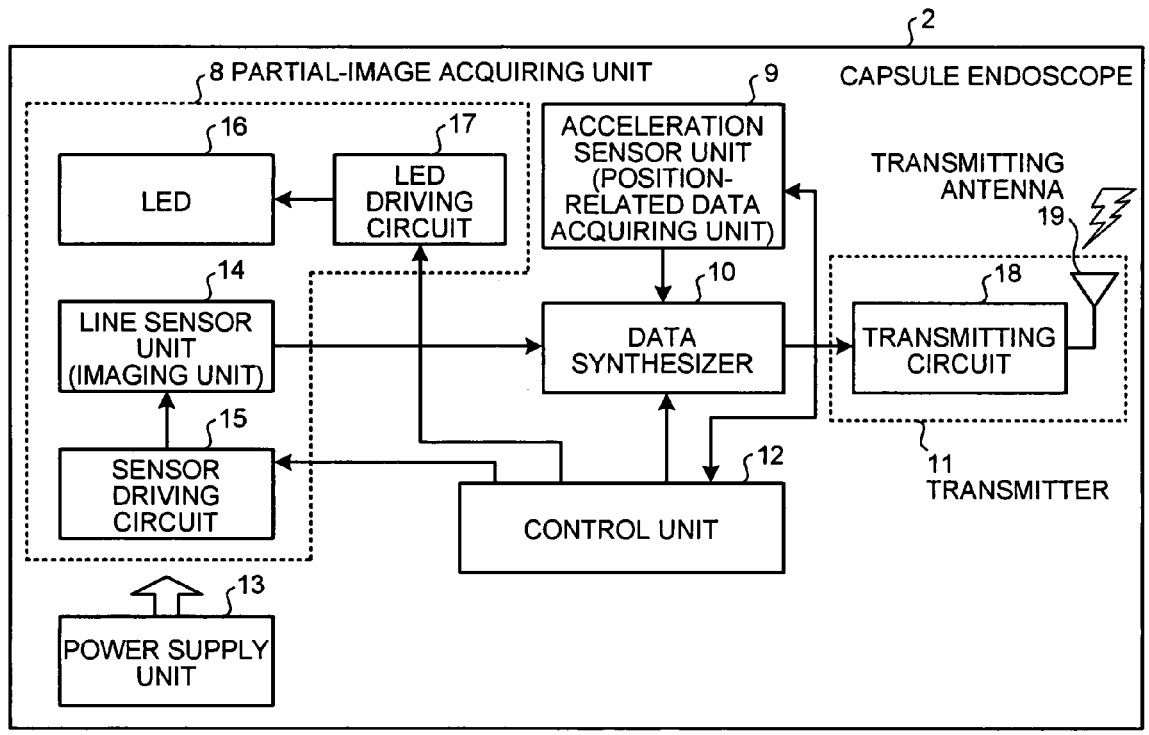
FIG. 2 is a typical block diagram showing an internal configuration of a capsule endoscope included in the in-vivo image acquiring system.

The capsule endoscope 2 will next be described. FIG. 2 is a block diagram typically showing the relationship among constituent elements of the capsule endoscope 2. As shown in FIG. 2, the capsule endoscope 2 includes a partial-image acquiring unit 8 that acquires a partial image, an acceleration sensor unit 9 that detects position related data constituted by acceleration data and the like on the capsule endoscope 2 when the capsule endoscope 2 moves in the body of the subject 1, and a data synthesizer 10 that generates overall-image generation data based on the position related data detected by the acceleration sensor unit 9. The capsule endoscope 2 also includes a transmitter 11 that transmits a radio signal including the overall-image generation data synthesized by the data synthesizer 10, a control unit 12 that controls driven states of the partial-image acquiring unit 8, the acceleration sensor unit 9, the data synthesizer 10, and the transmitter 11, and a power supply unit 13 that supplies driving power to the respective constituent elements of the capsule endoscope 2.

The partial-image acquiring unit 8 is to acquire a partial image that is an image related to a partial area of a predetermined imaging target in the body of the subject 1. Specifically, the partial-image acquiring unit 8 includes a line sensor unit 14 that functions as an imaging unit, a sensor driving circuit 15 that controls a driven state of the line sensor unit 14, an LED 16 that outputs an illumination light when the line sensor 14 picks up the partial image, and an LED driving circuit 17 that controls a driven state of the LED 16. Since specific configurations of the line sensor unit 14 and the LED 16 are described later in detail, they will not be described herein.

The acceleration sensor unit 9 functions as an example of a position-related-data acquiring unit as set forth in the claims, and is to detect position related data necessary when a position of the capsule endoscope is calculated at the time of acquiring each partial image. In this embodiment, acceleration data, which is data on an acceleration of the capsule endoscope 2, and time data, which is data on time when the acceleration data is detected are used as the position related data. Specifically, the acceleration sensor unit 9 is configured to include an acceleration detection mechanism such as a small-sized gyroscope and a time detection mechanism, and functions to output the detected acceleration data and time data to the data synthesizer 10 and the control unit 12 as the position related data.

The data synthesizer 10 is to generate overall-image generation data. Specifically, the data synthesizer 10 functions to generate the overall-image generation data based on the partial image data input from the partial-image acquiring unit 8 and the position related data input from the acceleration sensor unit 9, and to output the overall-image generation data to the transmitter 11.

The transmitter 11 is to radio-transmit the overall-image generation data generated by the data synthesizer 10 after performing a necessary processing on the overall-image generation data. Specifically, the transmitter 11 includes a transmitting circuit 18 that performs a modulation processing or the like on the input data, and a transmitting antenna 19 for transmitting the radio signal output from the transmitting circuit 18.

The control unit 12 is to control the driven states and the like of the partial-image acquiring unit 8 and the like included in the capsule endoscope 2. Specifically, the control unit 12 functions to exercise ordinary control over these constituent elements, and also functions to drive the partial-image acquiring unit 8, the acceleration sensor unit 9, and the data synthesizer 10 while synchronizing them with one another.

Furthermore, the control unit 12 functions to calculate a moving velocity of the capsule endoscope 2 based on the position related information input from the acceleration sensor unit 9, and to control the driven state of the partial-image acquiring unit based on the calculated moving velocity. Specific contents of these functions will be described later in detail.

Figure 3:
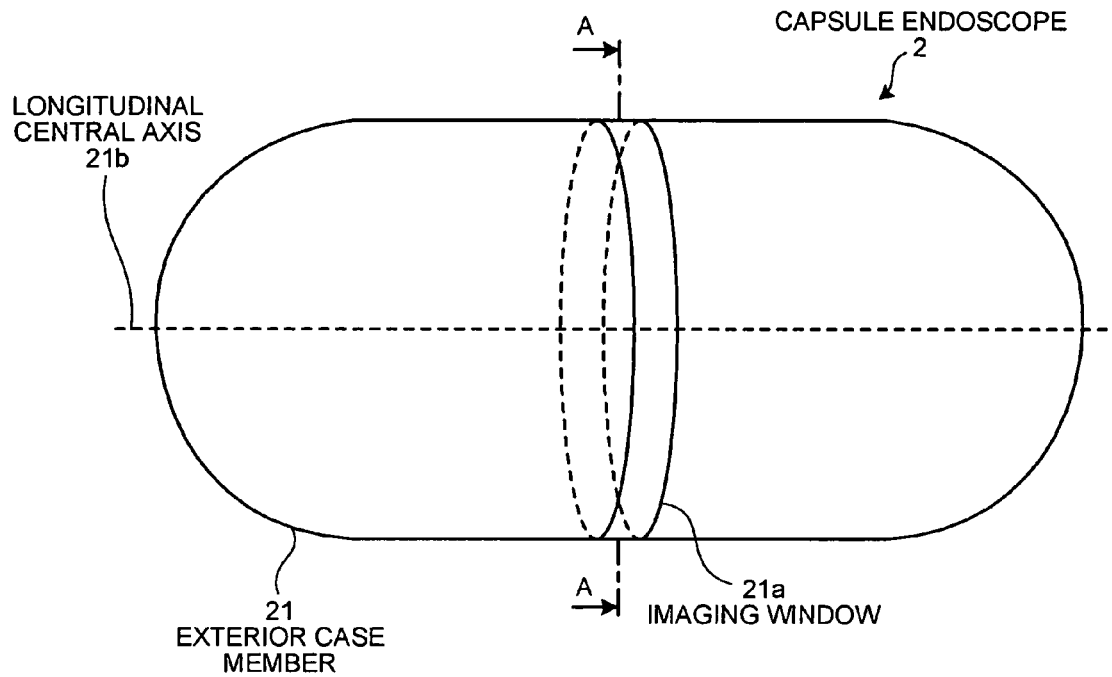
FIG. 3 is a pattern diagram showing an exterior of the capsule endoscope.
Figure 4:
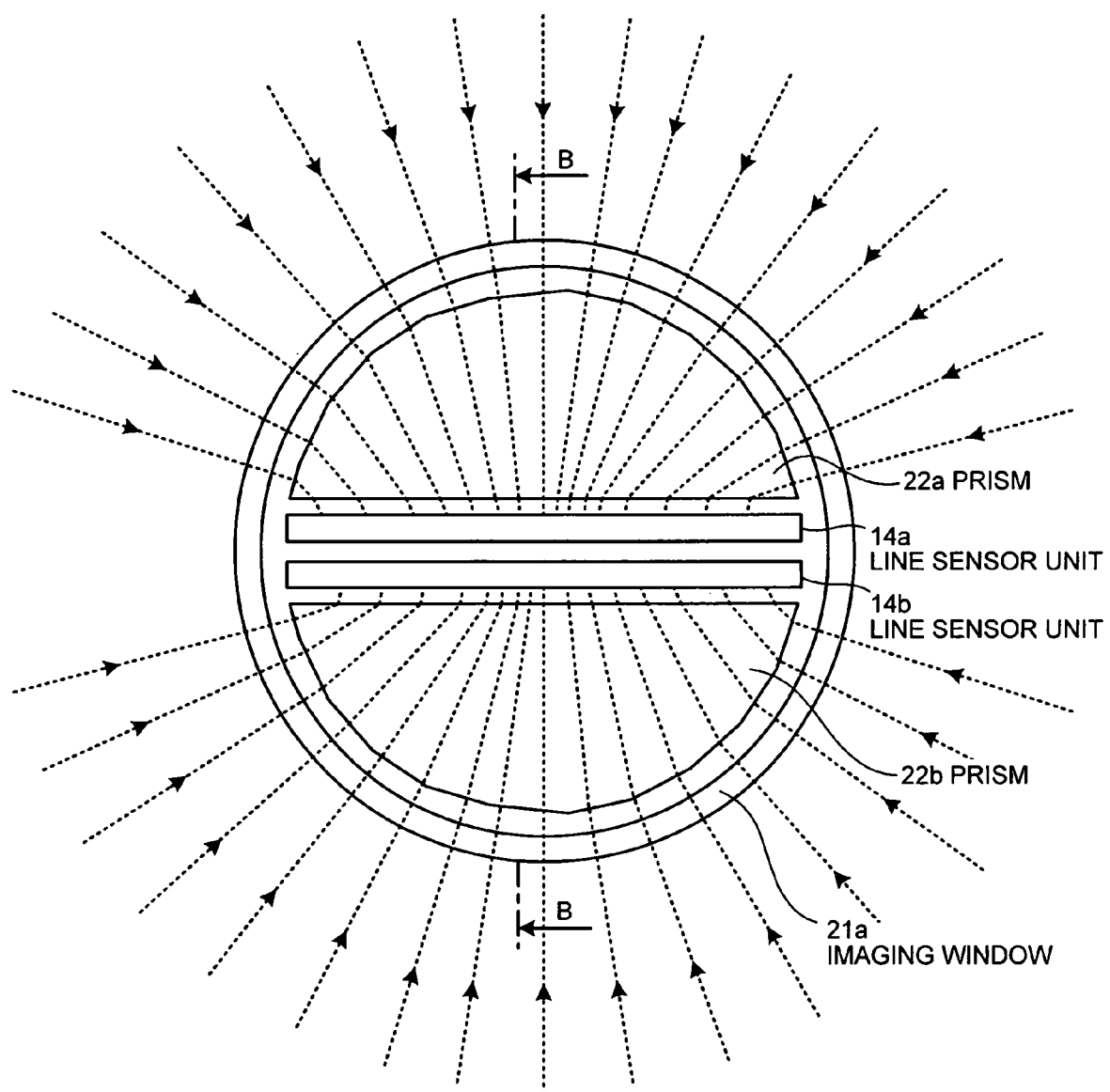
FIG. 4 is a cross-sectional view taken along a line A-A of FIG. 3.
Figure 5:
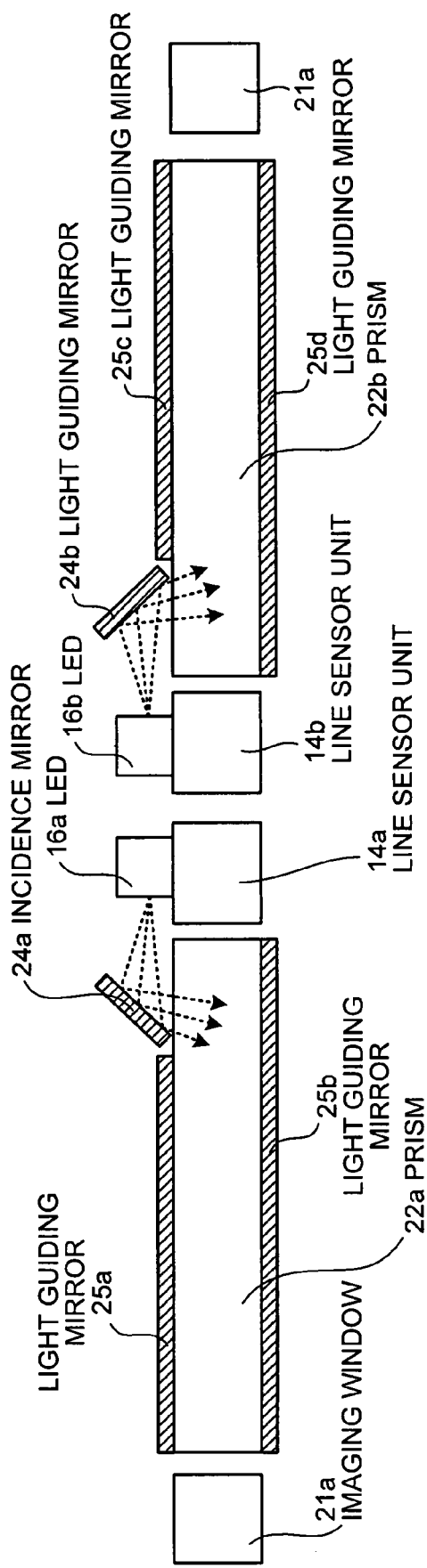
FIG. 5 is a cross-sectional view taken along a line B-B of FIG. 4.

Specific configurations of the line sensor unit 14 and the LED 16 that constitute the partial-image acquiring unit 8 will next be described. FIG. 3 is a pattern diagram showing an exterior of the capsule endoscope 2, FIG. 4 is a cross-sectional view taken along a line A-A of FIG. 3, and FIG. 5 is a cross-sectional view taken along a line B-B of FIG. 4. The line sensor unit 14 and the like will be described using these drawings.

As shown in FIG. 3, the exterior of the capsule endoscope 2 is formed by an exterior case member 21 for including the respective constituent elements shown in FIG. 2. The exterior case member 21 is made of a biomaterial or the like, and is partially structured to include an imaging window 21a made of a member exhibiting optical transparency. The imaging window 21a is to input external light to the line sensor unit 14, and is specifically formed to have a field of vision of 360° axially about a longitudinal central axis 21b of the exterior case member 21.

The line sensor unit 14 is arranged at a position at which the light input through the imaging window 21a can arrive at the line sensor unit 14 in the exterior case member 21. Specifically, as shown in FIG. 4, which is the cross-sectional view taken along the line A-A of FIG. 3, line sensor units 14a and 14b are arranged on a plane which includes the line A-A and which is orthogonal to a longitudinal central axis 21b. Furthermore, to image the light input to light-receiving surfaces of the line sensor units 14a and 14b through the imaging window 21a, the capsule endoscope 2 is configured to arrange prisms 22a and 22b in areas between the line sensors 14a and 14b and the imaging window 21a, respectively.

Each of the line sensor units 14a and 14b is configured so that a plurality of photoelectric conversion mechanisms such as photodiodes is arranged in a one-dimensional array, and includes a mechanism of outputting an electric signal obtained by each photoelectric conversion mechanism if necessary. The line sensor units 14a and 14b include the light-receiving surfaces opposite to surfaces facing each other, and function to convert the light input to the respective light-receiving surfaces from the outside into electric signals. Data acquired by photoelectric conversion processing performed by the line sensor units 14a and 14b is synthesized by a predetermined circuit (not shown), and output to the data synthesizer 10 as the partial image data corresponding to a range of 360° axially around the longitudinal central axis 21b to correspond to the field of vision prescribed by the imaging window 21a.

The prisms 22a and 22b are to form images of lights input through the imaging window 21a on the light-receiving surfaces of the respective line sensor units 14a and 14b. Specifically, the prisms 22a and 22b function to perform refraction and imaging on the input lights passed through the imaging window 21a, thereby forming images of tissues in the body of the subject 1 in an area located on extension of a direction perpendicular to the longitudinal central axis 21b, with respect to the imaging window 21a on the light-receiving surfaces of the respective line sensor units 14a and 14b.

A cross-sectional structure taken along the line B-B of FIG. 4 will be described. As shown in FIG. 5, each of the prisms 22a and 22b also functions as a light guide path for the illumination light output from the LED 16. Specifically, the lights output from LEDs 16a and 16b arranged on the line sensor units 14a and 14b are reflected by incidence mirrors 24a and 24b arranged near the line sensor units 14a and 14b, whereby the lights are incident on the prisms 22a and 22b, respectively. Furthermore, light guiding mirrors 25a to 25d are arranged on upper and lower surfaces of the prisms 22a and 22b, respectively, and the illumination lights incident on the prisms 22a and 22b are reflected by the light guiding mirrors 25a to 25d, whereby the illumination lights are propagated through the prisms 22a and 22b and finally output to the outside through the imaging window 21a.

Figure 6:
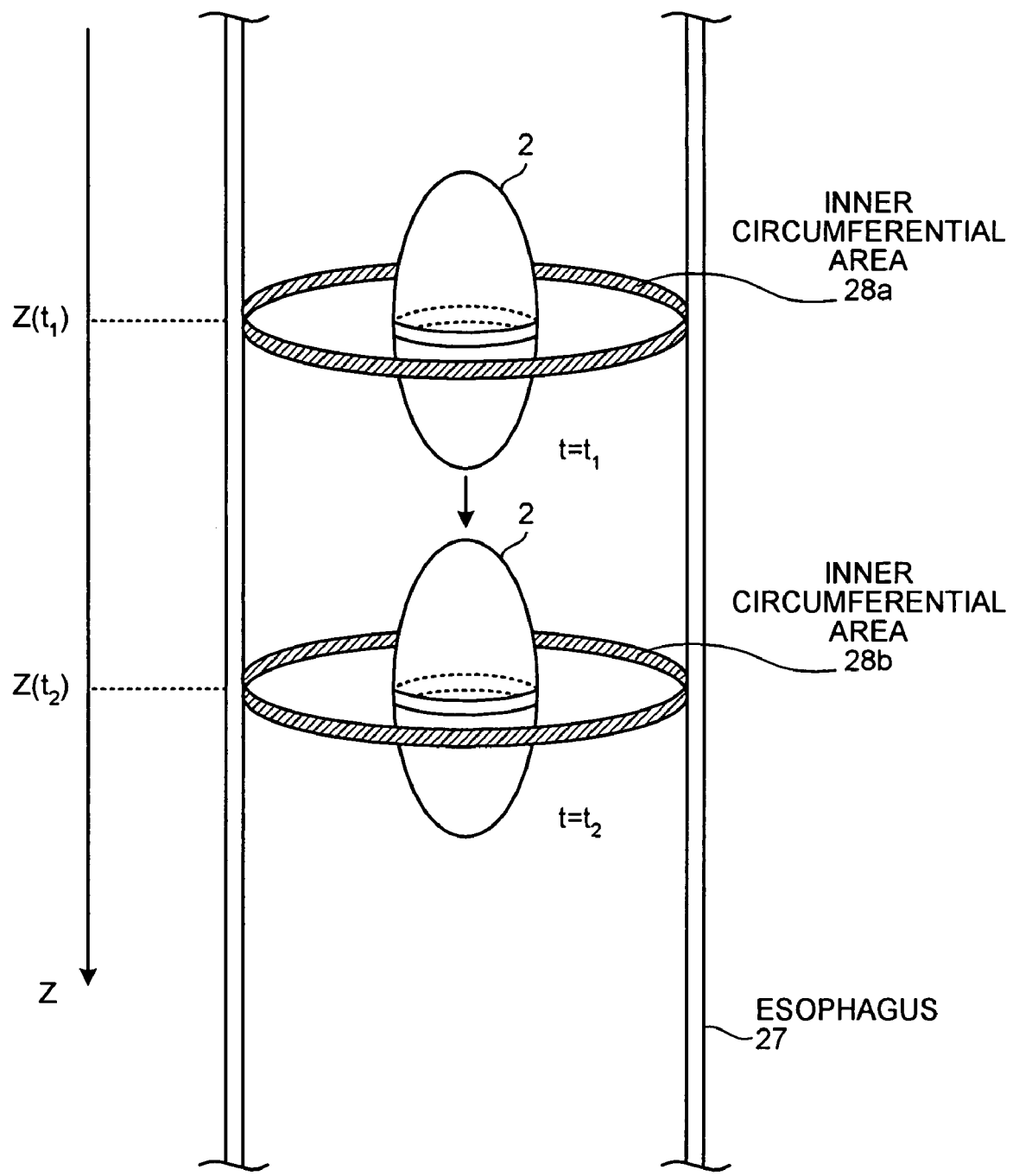
FIG. 6 is a pattern diagram for explaining an operation performed by the capsule endoscope for acquiring partial image data.

An imaging operation performed by the capsule endoscope 2 for picking up partial images will be described. The capsule endoscope 2 functions to sequentially acquire partial image data corresponding to different parts according to movement of the capsule endoscope 2 in the body of the subject 1. FIG. 6 is a schematic typically showing the imaging operation performed by the capsule endoscope 2 when the capsule endoscope 2 passes through the esophagus as an example of the imaging operation. The operation performed by the capsule endoscope 2 will now be described with reference to FIG. 6.

As already described, the line sensor units 14a and 14b included in the capsule endoscope 2 function to pick up the images of intra-subject tissues located in the direction perpendicular to the moving direction of the capsule endoscope 2 (i.e., perpendicular to the extension direction of the longitudinal central axis 21b) by the functions of the imaging window 21a and the prisms 22a and 22b. Accordingly, at time t1, the capsule endoscope 2 picks up an image of an inner circumferential area 28a out of an inner wall of an esophagus 27, which area is located in the direction perpendicular to the moving direction of the imaging window 21a and which area is identical in width to the imaging window 21a in the moving direction as the partial image data.

Thereafter, the capsule endoscope 2 moves in the esophagus 27 by the action of gravitation, and specifically moves to a position $Z(t2)$ different from a position $Z(t_1)$ where the capsule endoscope 2 is located at the time t1, at time $t_2$. Accordingly, an area located in the direction perpendicular to the moving direction of the capsule endoscope 2, with respect to the imaging window 21a is an inner circumferential area 28b different from the inner circumferential area 28a, and the line sensor units 14a and 14b newly acquire partial image data on the images of the inner circumferential area 28b, respectively. Likewise, the partial image data corresponding to different inner circumferential areas is sequentially acquired according to the movement of the capsule endoscope 2.

Meanwhile, the capsule endoscope 2 acquires position related data related to the positional relationship among the different inner circumferential areas to follow the operation for acquiring the partial images. Specifically, the acceleration sensor unit 9 included in the capsule endoscope 2 detects an acceleration of the capsule endoscope 2 at the time when each partial image is acquired as acceleration data. Likewise, the acceleration sensor unit 9 detects times $t_1$, $t_2$, . . . when the respective acceleration data is detected (=times when the respective partial image data is acquired) as time data, and outputs the position related data based on the acceleration data and the time data to the data synthesizer 10 and the control unit 12.

In this manner, when passing through the interior of the subject 1, e.g., the esophagus 27, the capsule endoscope 2 acquires a plurality of partial images by imaging partial areas (such as the inner circumferential areas 28a and 28b) of the imaging target (which is the esophagus 27 in the example of FIG. 6) and the position related data (which is information on the accelerations and the times during pickup of the respective partial images in this embodiment) for calculating the positional relationship among the partial images. Furthermore, the data synthesizer 10 generates the overall-image generation data based on these data, and the radio signal including the overall-image generation data is transmitted by the transmitter 11 to the receiving apparatus 3.

Figure 7:
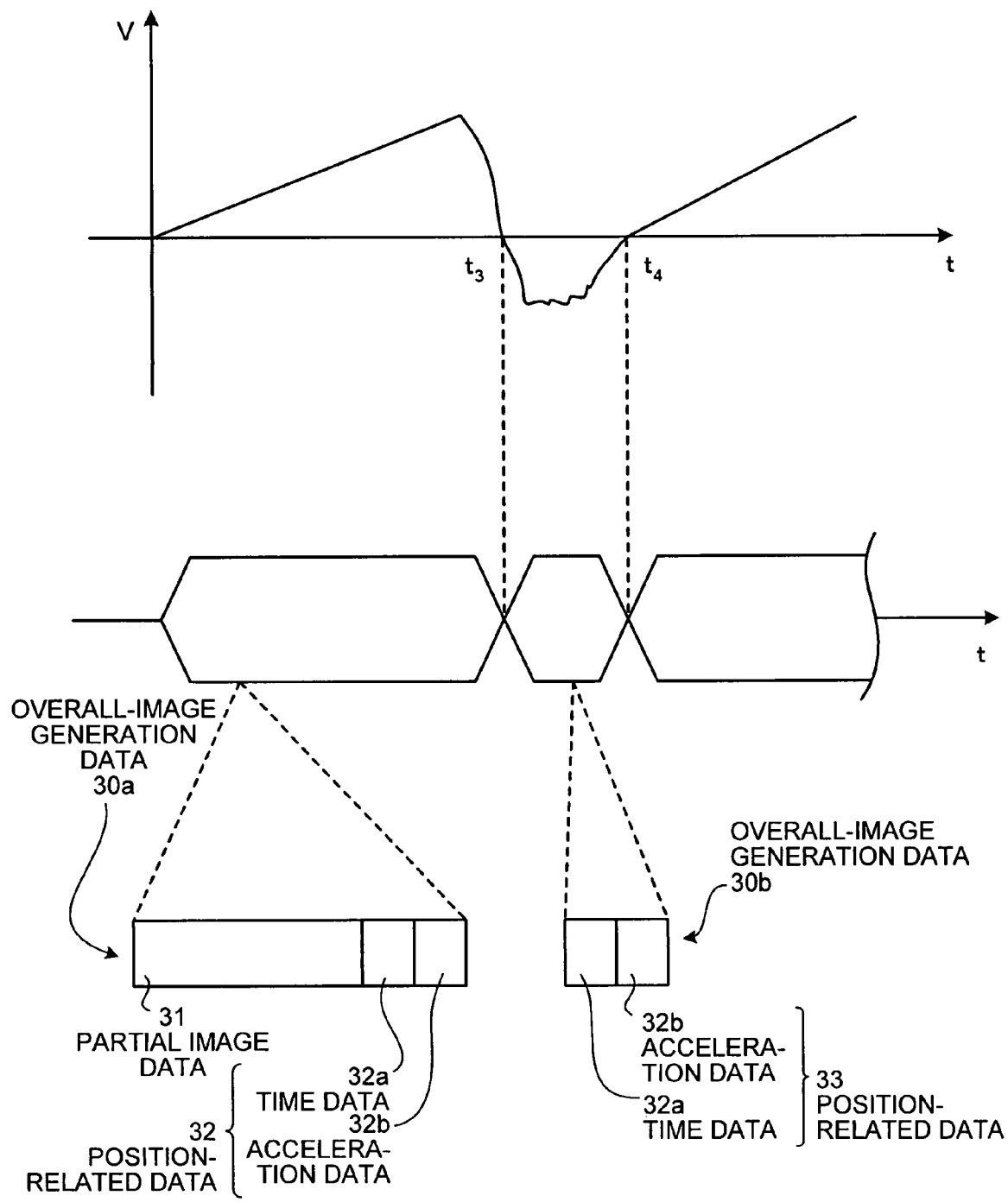
FIG. 7 is a pattern diagram showing contents of overall-image generation data.

FIG. 7 is a pattern diagram showing a configuration of the overall-image generation data generated by the data synthesizer 10. Referring to FIG. 7, a graph with a horizontal axis indicating time t and a vertical axis indicating velocity v is a typical graph showing an example of a temporal change in the moving velocity of the capsule endoscope 2, and the data synthesizer 10 generates the overall-image generation data different in aspect to correspond to the velocity changes shown in the graph. It is to be noted that the velocity v indicated by the vertical axis of the graph in the ordinary moving direction of the capsule endoscope 2 is assumed as a positive velocity. Specifically, the velocity in the direction in which the capsule endoscope 2 sequentially moves from the oral cavity toward the esophagus, the stomach, the small intestine, and the large intestine is positive, and the velocity in the opposite direction thereto is negative. The same shall apply hereafter.

Specifically, if the velocity v of the capsule endoscope 2 is positive, that is, $t \leq t_3$ or $t_4 \leq t$, the data synthesizer 10 generates overall-image generation data 30a, and if the velocity v is negative, that is, $t_3 < t < t_4$, the data synthesizer 10 generates overall-image generation data 30b different in constitution from the overall-image generation data 30a.

The overall-image generation data 30a is constituted by partial image data 31 and position related data 32 corresponding to the partial image data 31. The partial image data 31 is image data corresponding to each of the inner circumferential areas 28a, 28b and the like, and the position related data 33 is data used when the position of the imaging target area corresponding to the partial image data 31 is to be identified. Specifically, the position related data 32 is constituted by time data 32a indicating time when the partial image data 31 is picked up, and acceleration data 32b indicating a value of the acceleration of the capsule endoscope 2 at that time.

On the other hand, the overall-image generation data 30b is formed only by the position related data 33. Since the velocity of the capsule endoscope 2 is negative in a time zone of $t_3 < t < t_4$, the partial-image acquiring unit 8 does not pick up any partial images in this time zone. Therefore, no partial image data is included in the overall-image generation data 30b generated by the data synthesizer 10. It is to be noted that the position related data 33 is constituted by time data 33a and acceleration data 33b similarly to the position related data 32.

Figure 8:
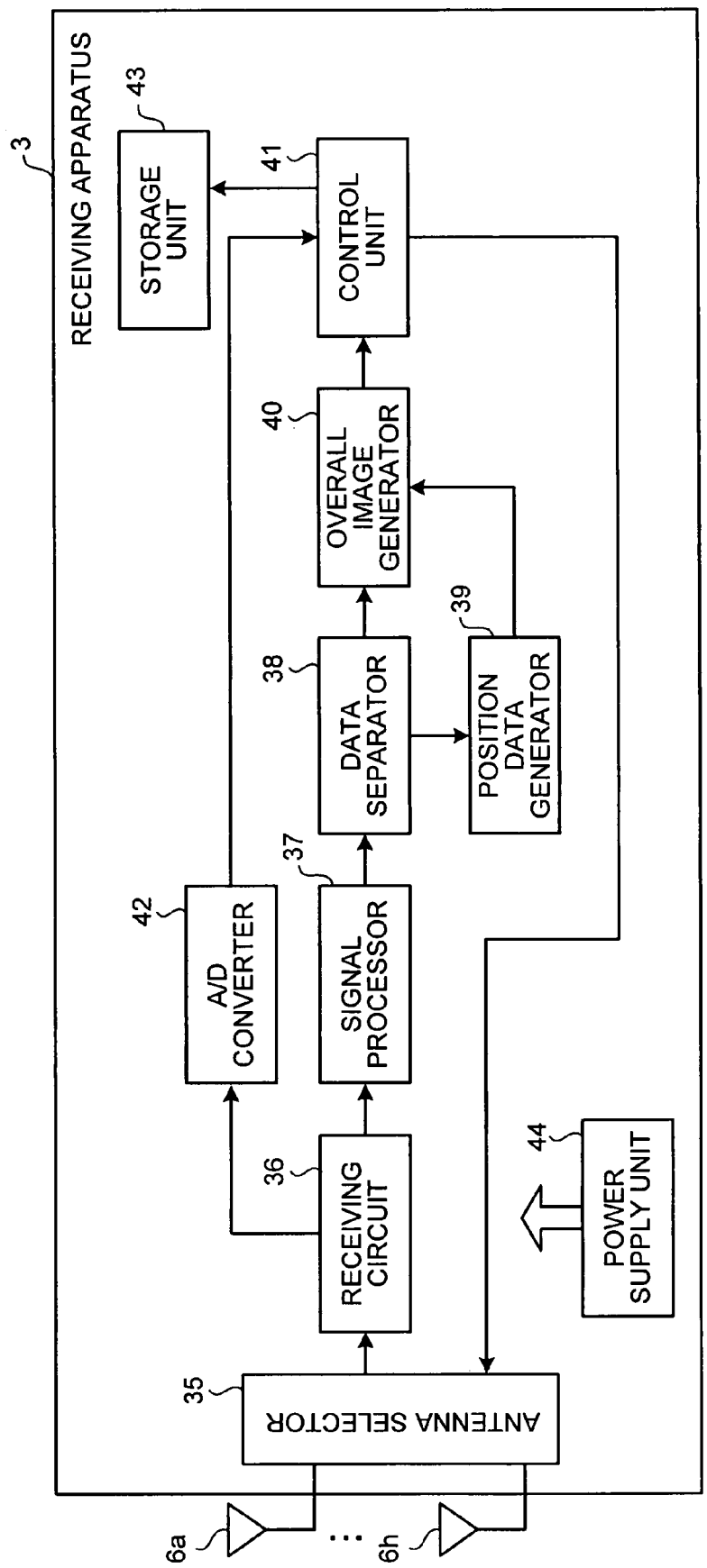
FIG. 8 is a typical block diagram showing an internal configuration of a receiving apparatus.

The receiving apparatus 3 that receives radio signals including the overall-image generation data 30a and 30b and that generates overall image data will next be described. FIG. 8 is a typical block diagram showing a configuration of the receiving apparatus 3.

As shown in FIG. 8, the receiving apparatus 3 includes an antenna selector 35 that selects one antenna suitable for receiving the radio signal from among the receiving antennas 6a to 6h, a receiving circuit 36 that perform a processing such as a demodulation processing on the radio signal received through the receiving antenna 6 selected by the antenna selector 35, and a signal processor 37 that extracts the overall-image generation data from the signal output from the receiving circuit 36. The receiving apparatus 3 also includes a data separator 38 that separates the partial image data and the position related data included in the overall-image generation data input from the signal processor 37 from each other and that outputs the partial image data and the position related data, a position data generator 39 that generate position data based on the position related data output from the data separator 38, and an overall image generator 40 that generates an overall image of the imaging target based on the partial image data output from the signal processor 37 and the position data output from the position data generator 39. Furthermore, the receiving apparatus 3 includes a control unit 41 that controls driven states and the like of the respective constituent elements of the receiving apparatus 3, an A/D converter 42 that converts a received strength signal output from the receiving circuit 36 into a digital signal and that outputs the digital signal to the control unit 41, a storage unit 43 that stores the overall image data generated by the overall-image generator 40, and a power supply unit 44 that supplies driving power to the respective constituent elements.

The antenna selector 35 selects an antenna suitable for receiving the radio signal from among the receiving antennas 6a to 6h. Specifically, the antenna selector 35 functions to select the predetermined receiving antenna 6 under control of the control unit 41, and to output the radio signal received through the selected receiving antenna 6 to the receiving circuit 36.

The receiving circuit 36 functions to perform a predetermined processing such as a demodulation processing on the radio signal received through the selected receiving antenna 6. The receiving circuit 36 also functions to output an analog signal corresponding to the strength of the received radio signal to the A/D converter 42.

The signal processor 37 functions to extract predetermined data from the signal on which the receiving circuit 36 has performed the predetermined processing. Specifically, the signal processor 37 functions to extract the overall-image generation data generated by the data synthesizer 10 included in the capsule endoscope 2 from the signal output from the receiving circuit 36.

The data separator 38 functions to separate the partial image data and the position related data included in the overall-image generation data output from the signal processor 37 from each other. The partial image data separated by the data separator 38 is output to the overall-image generator 40 whereas the position related data is output to the position data generator 39.

The position data generator 39 functions to generate the position data as information indicating the position of the capsule endoscope 2 when the corresponding partial image data is picked up based on the position related data or, more properly, information indicating the position of the partial-image acquiring unit 8 included in the capsule endoscope 2. Since the acceleration data and the time data are assumed as the position related data in this embodiment, the position data generator 39 calculates the position of the partial-image acquiring unit 8 when the partial image data is acquired by performing twice, for example, a temporal integration processing on the acceleration data, and outputs the calculated position to the overall-image generator 40 as the position data. If the acceleration data is to be subjected to the temporal integration, more accurate position data is generated by using even the acceleration data on the time when the partial-image acquiring unit 8 does not acquire any partial images.

The control unit 41 is to exercise ordinary control over the respective constituent elements and overall control over operations including an antenna selecting operation performed by the antenna selector 35. Specifically, the control unit 41 functions to transfer the overall image data acquired by the overall-image acquiring unit 40 to the storage unit 43 to store the overall image data in the storage unit 43, and to decide the receiving antenna 6 to be used based on the digital signal (e.g., an RSSI (Received Signal Strength Indicator) corresponding to the received strength and to instruct the antenna selector 35 to select the receiving antenna 6.

The storage unit 43 is to store the overall image data generated by the overall-image generator 40. As a specific configuration of the storage unit 43, the storage unit 43 can store therein data per se by including a memory or the like. However, in this embodiment, the storage unit 43 functions to write data to the portable recording medium 5.

The overall-image generator 40 and the overall image data generated by the overall-image generator 40 will be described. The overall-image generator 40 generates the overall image of the imaging target based on the partial image data and the position related data corresponding to the position data (more properly, the position data generated based on the position related data). Specifically, the overall-image generator 40 functions to generate the overall image data by arranging a plurality of partial image data on a predetermined image space to correspond to respective imaging positions described in the position data.

As contents of the generated overall image data, the contents can be simply such that a plurality of partial images is arranged according to the positional relationship. In this embodiment, however, the overall image data is subjected to a predetermined image processing, thereby facilitating diagnosis by the doctor or the like.

Figure 9:
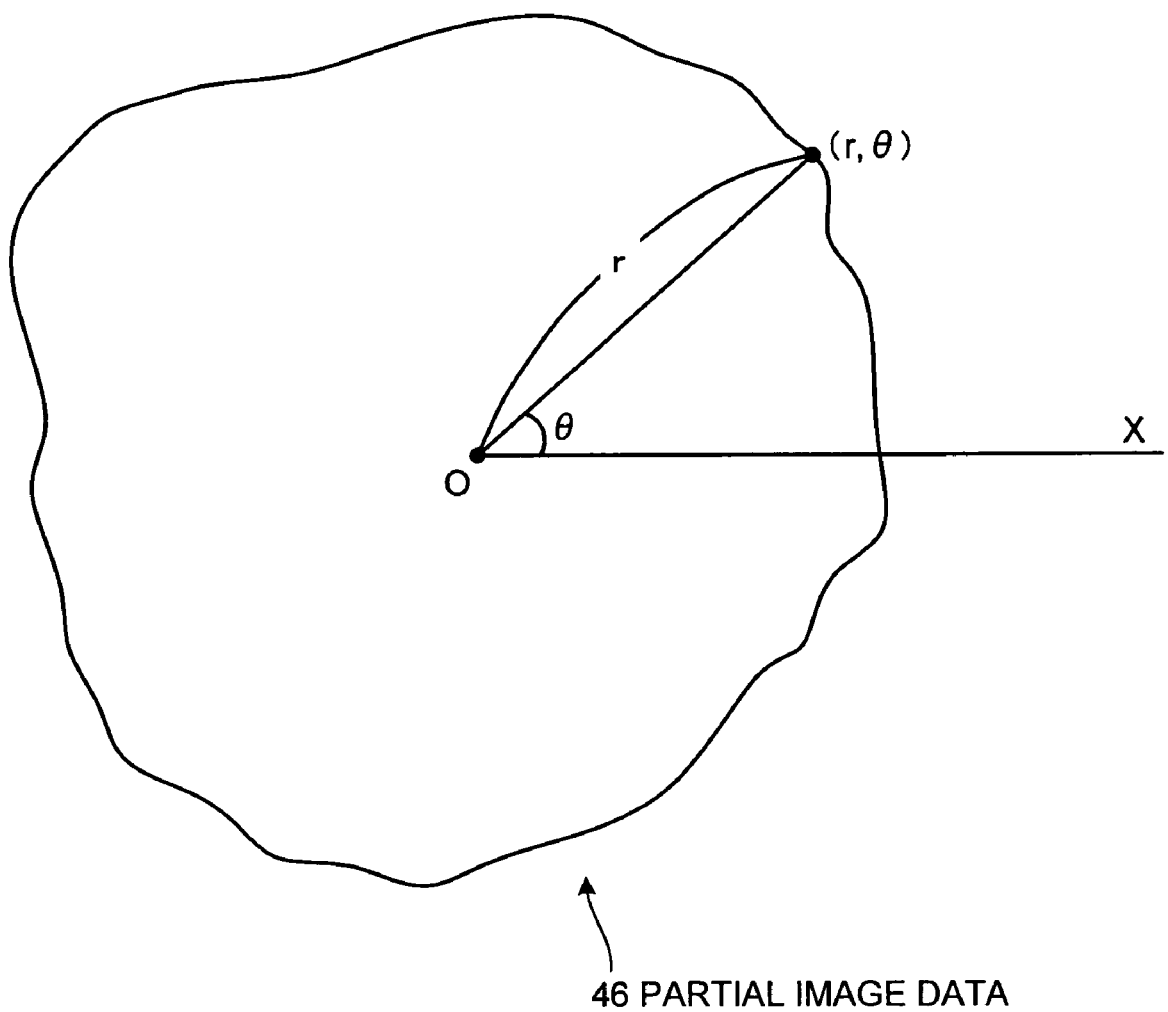
FIG. 9 is a pattern diagram showing contents of partial image data.

FIG. 9 is a pattern diagram showing partial image data 46 that has been subjected to the image processing by the overall-image generator 40 prior to generation of the overall image data. As shown in FIG. 9, the partial image data 46 has a data configuration indicating a brightness of each corresponding part of an inner circumferential area 28. Namely, the partial image data 46 is configured by a content in which a position of each part of the inner circumferential area 28 is expressed by an angle θ relative to a predetermined reference axis X and in which the brightness of the part is expressed according to a distance r from an origin O. It is to be noted that the distance r is defined by, for example, a reciprocal of the brightness of each part, and that, if the distance r is larger, this means that the brightness is lower.

In this manner, the overall-image generator 40 generates the partial image data 46 by performing the predetermined image processing prior to generation of the overall image data. Furthermore, the overall-image generator 40 generates the overall image data by arranging a plurality of partial image data 46 on the predetermined image space according to the corresponding position data.

Figure 10:
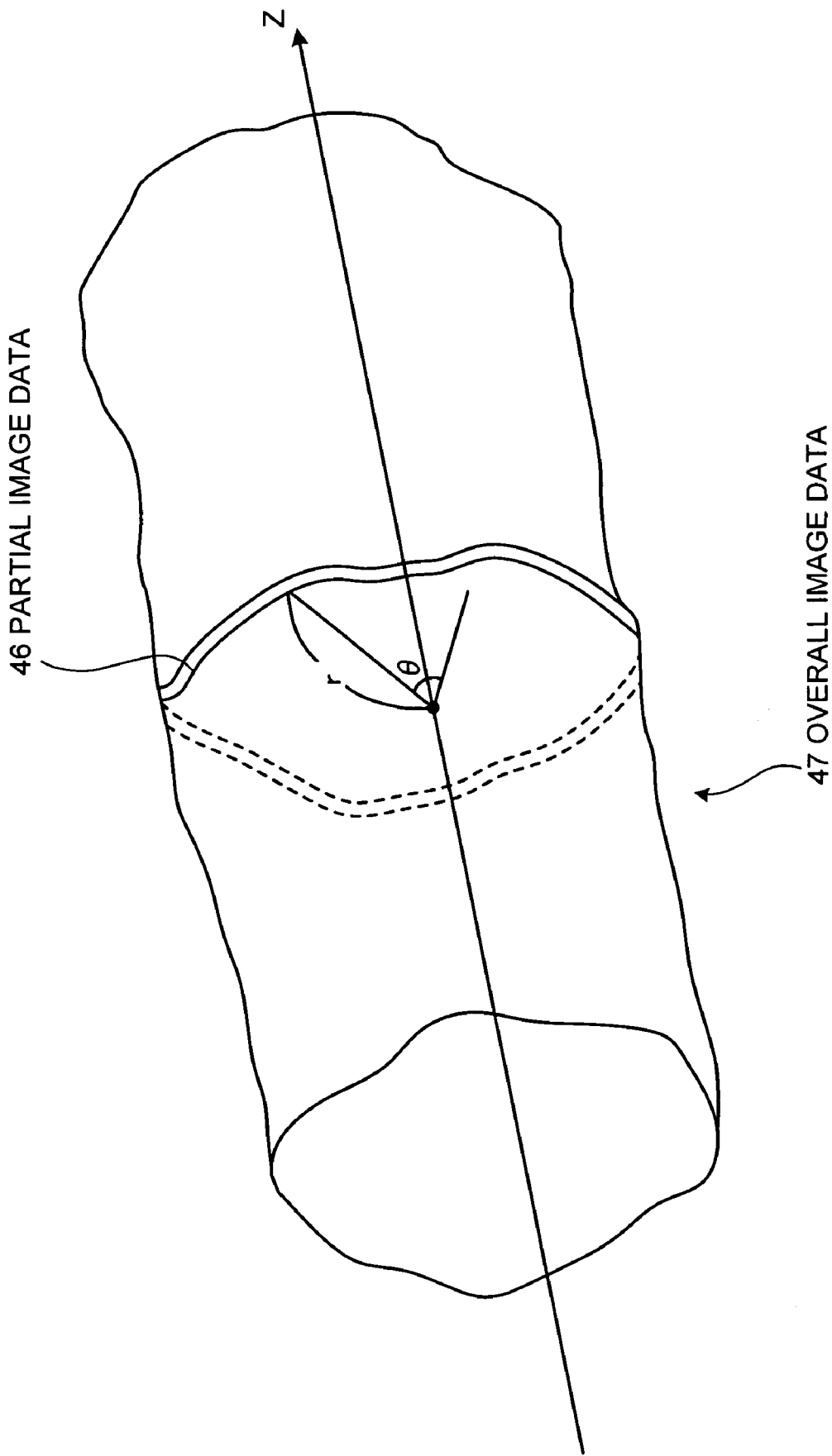
FIG. 10 is a pattern diagram showing contents of overall image data.

FIG. 10 is a pattern diagram showing a configuration of overall image data 47 generated by the overall-image generator 40. As shown in FIG. 10, the overall image data 47 is configured so that a plurality of partial image data 46 is arranged with reference to a z-axis corresponding to the moving direction of the capsule endoscope 2. More specifically, each of the partial image data 46 is arranged in a state in which a predetermined position on the z-axis is set as an origin, and an order of arranging the partial image data 46 is set to correspond to the positions of the line sensor unit 14 in the subject 1 during imaging. In the example of FIG. 10, the position data is used only to decide the arrangement order of the partial image data 46, and the partial image data 46 is continuously arranged. Alternatively, the partial image data 46 can be arranged, for example, in a state of separating the partial image data 46 according to the distance between the adjacent partial image data calculated based on the position data.

By configuring the overall image data 47 as shown in FIG. 10, the overall image of the imaging target (e.g., the esophagus 27) is generated. The overall image data 47 is output to the portable recording medium 5 through the storage unit 43, output to the display device 4 through the portable recording medium 5, and displayed on a screen of the display device 4 in a manner shown in FIG. 10, whereby the overall image data 47 is used for the diagnosis or the like by the doctor.

Advantages of the in-vivo image acquiring system according to this embodiment will be described. The in-vivo image acquiring system according to this embodiment is configured to generate the overall image based on the partial images acquired by the partial-image acquiring unit 8 and the position related data corresponding to the respective partial images. Therefore, even if the image is an image of the entire imaging target present in a wide range, it is advantageously possible to acquire image data using the imaging unit having a narrow imaging field of vision. Namely, since the in-vivo image acquiring system is configured to acquire not only the partial image data but also the corresponding position related data in this embodiment, it is possible to grasp the positional relationship among a plurality of partial image data and to generate the overall image data using the partial image data. Accordingly, even if a wide range is to be imaged, there is no need to provide an imaging unit having a wide imaging field of vision, whereby the in-vivo image acquiring system can be realized at low cost.

Specifically, by providing the line sensor unit 14 that includes the photoelectric conversion mechanisms arranged in the one-dimensional array as the imaging unit, the in-vivo image in relation to the wide range can be acquired. Furthermore, therefore, the in-vivo image acquiring system according to this embodiment does not need to include a conventional imaging unit including many photoelectric conversion mechanisms arranged in a two-dimensional array, and it is advantageously possible to make the imaging unit small in size and reduce manufacturing cost.

Moreover, in this embodiment, the capsule endoscope 2 has a property of moving in the body of the subject 1 according to the action of an external force such as the gravitation or the peristaltic movements of the digestive organs. Due to this, the partial-image acquiring unit 8 can acquire the partial images related to different parts of the imaging target by performing the imaging operation at predetermined time intervals a plurality of times, and there is no need to provide a mechanism for changing the field of vision of the partial-image acquiring unit 8 to image the different parts, a moving mechanism for changing the position of the capsule endoscope 2, and the like. Accordingly, if the in-vivo image acquiring system is configured by using the capsule endoscope 2 as described in this embodiment, it is advantageously possible to configure the in-vivo image acquiring system with the simple configuration without the moving mechanism and the like.

Moreover, the in-vivo image acquiring system according to this embodiment can advantageously acquire the overall image of the imaging target while suppressing an increase in a data amount of acquired images. The problems with the conventional capsule endoscope system include the problem that the imaging rate is restricted so as to suppress an increase in power consumption and that it is, therefore, difficult to acquire the overall image of the imaging target. The in-vivo image acquiring system according to this embodiment, by contrast, can change the number of partial image data used to generate the overall image data by adjusting, for example, imaging intervals, adjust the amount of data transmitted from the capsule endoscope 2 by changing the number of partial image data, and reduce the number of partial image data sufficiently to suppress the power consumption. However, even if the number of partial image data is reduced, the overall image data can be generated although resolution is slightly lowered. The in-vivo image acquiring system according to this embodiment can, therefore, advantageously acquire the overall image of the imaging target while satisfying the condition of reduction in power consumption.

Moreover, since the in-vivo image acquiring system according to this embodiment adopts the configuration in which the driven state of the partial-image acquiring unit 8 is controlled according to the moving velocity of the capsule endoscope 2 in the body of the subject 1, the in-vivo image acquiring system can advantageously prevent acquiring unnecessary partial images. Specifically, the in-vivo image acquiring system according to this embodiment functions to stop driving the partial-image acquiring unit 8 by the control unit 12 when the moving velocity of the capsule endoscope 2 becomes negative. Since the fact that the moving velocity becomes negative means that the capsule endoscope 2 returns to the area for which the partial image has been already acquired, it is less significant to pick up a partial image from viewpoints of generation of the overall image in this case. In the embodiment, therefore, if the moving velocity is negative, the pickup of the partial image is stopped, whereby it is advantageously possible to prevent acquiring unnecessary partial images, reduce the power consumption of the partial-image acquiring unit 8, and reduce the power consumption of the transmitter 11 by reducing the amount of transmitted data. With a view of exhibiting these advantages, the imaging rate can be changed according to, for example, the moving velocity besides the instance in which the moving velocity is negative.

Furthermore, in the in-vivo image acquiring system according to the embodiment, the overall-image generator 40 generates a three-dimensional image corresponding to the brightness of each part as the overall image data. For example, if a foreign matter such as a tumor is present in the imaging target, the foreign matter is generally imaged at a different brightness from those of the other parts. By adopting the configuration in which the brightness of each part is expressed as the overall image data, therefore, it is advantageously possible to constitute the in-vivo image acquiring system that generates the overall image data capable of facilitating the diagnosis by the doctor or the like.

The present invention has been described so far based on the embodiment; however, there is no need to interpret the present invention while only limiting the invention to the embodiment but a person having ordinary skill in the art could attain various embodiments, modifications and the like. For example, the position related data is constituted by the acceleration data and the time data in the embodiment. However, it is unnecessary to interpret the present invention while limiting the constitution of the position related data thereto but the position related data can be constituted by velocity data and the time data. In another alternative, the position related data can be constituted by information on the position of the capsule endoscope 2 at the time of imaging per se, and the position information on the capsule endoscope 2 can be used per se as the position related data by separately providing a mechanism for detecting the position of the capsule endoscope 2. In yet another alternative, the position related data can be constituted only by the time data as a simple configuration for the following reason. Even if only the time when each partial image data is picked up is acquired as the position related data, the arrangement order of the partial image data is known and the overall image data can be generated.

Moreover, in this embodiment, the data synthesizer 10 generates the overall-image generation data by integrating the partial image data with the position related data as shown in FIG. 7. However, there is no need to interpret the present invention while limiting the configuration of the capsule endoscope 2 to the configuration of generating the overall-image generation data. Namely, as evident from the foregoing, when the overall-image generator 40 is to generate the overall image data, the overall image data can be generated as long as the respective pieces of partial image data and the position data corresponding to each partial image data are known. Therefore, an identification code, for example, can be assigned to a header part of each of the partial image data and the position related data, and the partial image data and the position related data corresponding to the partial image data can be separately, independently transmitted while a common identification code is assigned to both the partial image data and the corresponding position related data. Even with this alternative configuration, the receiving apparatus can grasp the correspondence and generate the overall image data.

In the embodiment, the in-vivo image acquiring system constituted by the capsule endoscope 2, the receiving apparatus 3 and the like has been described. However, it is unnecessary to limit the physical configuration of the in-vivo image acquiring system to that described in the embodiment. Alternatively, an endoscope described in, for example, Japanese Patent Application Laid-Open No. 2004-188217 can be configured to arrange the partial-image acquiring unit on a tip end of an insertion unit and to arrange the overall-image generator in an operation unit. Namely, it suffices that the in-vivo image acquiring system according to the present invention includes, as minimum constituent elements, the mechanism of picking up partial images and an associating unit that makes the position related data on the position of the imaging mechanism during pickup of each partial image correspond to the partial image data, and preferably also includes a unit that generates the overall image based on the partial image data and the position related data. As a manner of transmitting, for example, the partial image data or the like, the transmission can be either radio transmission or wired transmission, and the in-vivo image acquiring system can be physically constituted by a single apparatus.

INDUSTRIAL APPLICABILITY

As stated so far, the in-vivo image acquiring system and the body-insertable apparatus according to the present invention are suitable for a medical observing apparatus inserted into the interior of a human body for observing a subject region, and particularly suitable for acquiring the overall image of a predetermined imaging target (subject region) in the body of the subject with simple configuration while suppressing increase in data amount.

The invention claimed is:

1. An in-vivo image acquiring system for acquiring an image of a predetermined imaging target in a body of a subject, comprising:
    a partial-image acquiring unit that acquires a plurality of partial image data corresponding to different parts of the imaging target in the body of the subject;
    a position-related-data acquiring unit that acquires position related data used to calculate a position of the partial-image acquiring unit in the body of the subject when the partial-image acquiring unit acquires each of the partial image data; and
    an overall-image generator that generates overall image data corresponding to an overall image of the imaging target using the plurality of partial image data based on the position related data, wherein
    the partial-image acquiring unit and the position-related-data acquiring unit are included in a capsule shaped body-insertable apparatus that transmits a predetermined radio signal and is inserted into an interior of the subject, and
    the partial-image acquiring unit includes a line sensor including a plurality of photoelectric conversion mechanisms arranged on a plane which is orthogonal to a longitudinal central axis of the body-insertable apparatus.

2. The in-vivo image acquiring system according to claim 1, wherein
    the overall-image generator is included in a receiving apparatus that receives the radio signal transmitted from the body-insertable apparatus and is arranged outside the subject when in use.

3. The in-vivo image acquiring system according to claim 2, wherein the body-insertable apparatus further includes a data synthesizer that generates overall-image generation data generated based on the partial image data and the position related data; and a transmitter that transmits the radio signal including the overall-image generation data generated by the data synthesizer, and wherein the receiving apparatus further includes a receiving circuit that performs a predetermined receiving processing on the radio signal transmitted by the transmitter and that outputs the extracted overall-image generation data to the overall-image generator.

4. The in-vivo image acquiring system according to claim 2, wherein the body-insertable apparatus further includes an exterior case that forms a capsule exterior and provides an imaging window which is formed on a part of the exterior case along a circumference about the longitudinal central axis of the capsule exterior, and the exterior case includes therein at least the partial-image acquiring unit and the position-related-data acquiring unit, and an outside light is input from a part of an inner periphery region of the imaging target to the partial-image acquiring unit through the imaging window.

5. The in-vivo image acquiring system according to claim 4, wherein the imaging window is formed between both ends of the exterior case along the longitudinal direction.

6. The in-vivo image acquiring system according to claim 5, wherein the body-insertable apparatus further includes an optical system that forms images of the outside light input through the imaging window on a light-receiving surface of the partial-image acquiring unit.

7. The in-vivo image acquiring system according to claim 6, wherein the partial-image acquiring unit further includes an illuminating unit that outputs an illumination light against a part of the inner periphery region of the imaging target when the partial-image acquiring unit acquires the partial image data corresponding to a part of the inner periphery region of the imaging target, and the optical system guides the illumination light output by the illuminating unit against a part of the inner periphery region of the imaging target.

8. The in-vivo image acquiring system according to claim 4, wherein the partial-image acquiring unit acquires the partial image data corresponding to a field of vision defined by the imaging window.

9. The in-vivo image acquiring system according to claim 1, wherein the position-related data acquiring unit includes an acceleration sensor unit that acquires at least acceleration data on a movement of the partial-image acquiring unit as the position related data.

10. The in-vivo image acquiring system according to claim 1, further comprising:

an acceleration sensor unit that detects an acceleration of the body-insertable apparatus, wherein the partial-image acquiring unit acquires the partial image data at plural times according to a detected result of the acceleration sensor unit.

11. The in-vivo image acquiring system according to claim 10, wherein an acquisition of the partial image data is not performed in a period in which a moving direction of the body-insertable apparatus becomes opposite.

12. A capsule shaped body-insertable apparatus insertable and movable in a body of a subject, comprising:

a partial-image acquiring unit that acquires a plurality of partial image data corresponding to different parts of an imaging target in the body of the subject according to a movement of the body-insertable apparatus in the body of the subject;

a position-related-data acquiring unit that acquires position related data necessary to calculate a position of the partial-image acquiring unit in the body of the subject when the partial-image acquiring unit picks up each of the partial image data;

a data synthesizer that generates overall-image generation data used to generate overall image data corresponding to an overall image of the imaging target, based on the partial image data and the position related data; and a transmitter that transmits a radio signal including the overall-image generation data, wherein the partial-image acquiring unit includes a line sensor including a plurality of photoelectric conversion mechanisms arranged on a plane which is orthogonal to a longitudinal central axis of the body-insertable apparatus.

13. The body-insertable apparatus according to claim 12, further comprising:

an exterior case that forms a capsule exterior and provides an imaging window which is formed on a part of the exterior case along a circumference about the longitudinal central axis of the capsule exterior, and the exterior case includes therein the partial-image acquiring unit, the position-related-data acquiring unit, the data synthesizer and the transmitter, and an outside light is input from a part of an inner periphery region of the imaging target to the partial-image acquiring unit through the imaging window.

14. The body-insertable apparatus according to claim 13, wherein the imaging window is formed between both ends of the exterior case along the longitudinal direction.

15. The body-insertable apparatus according to claim 13, further comprising:

an optical system, disposed in the exterior case, that forms images of the outside light input through the imaging window on a light-receiving surface of the partial-image acquiring unit.

16. The body-insertable apparatus according to claim 13, wherein the partial-image acquiring unit further includes an illuminating unit that outputs an illumination light against a part of the inner periphery region of the imaging target when the partial-image acquiring unit acquires the partial image data corresponding to a part of the inner periphery region of the imaging target, and the optical system guides the illumination light output by the illuminating unit against a part of the inner periphery region of the imaging target.

17. The body-insertable apparatus according to claim 13, wherein the partial-image acquiring unit acquires the partial image data corresponding to a field of vision defined by the imaging window.

18. An in-vivo image acquiring method for acquiring an image of a predetermined imaging target in a body of a subject, comprising:

inserting a capsule shaped body-insertable apparatus including an imaging unit and a radio communication unit into a body of a subject;

acquiring a plurality of partial image data corresponding to different parts of the imaging target in the body of the subject and a position-related-data associated with a positional relation between different parts among the imaging target; and generating overall image data corresponding to an overall image of the imaging target using a plurality of the partial image data, based on the acquired position-related-data, wherein the partial image data is acquired by a line sensor including a plurality of photoelectric conversion mechanisms arranged on a plane which is orthogonal to a longitudinal central axis of the body-insertable apparatus.

19. The in-vivo image acquiring method according to claim 18, further comprising:
receiving a plurality of the partial-image data and the position-related-data transmitted wirelessly from the body-insertable apparatus by a receiving apparatus disposed outside the body of the subject; and
generating the overall image data using a plurality of the partial-image data and the position-related-data received.

20. The in-vivo image acquiring method according to claim 19, wherein the partial-image data is acquired by inputting an outside light from a part of an inner periphery region of the imaging target to the imaging unit of the body-insertable apparatus through an imaging window of an exterior case, the imaging window being formed on a part of the exterior case along a circumference about the longitudinal central axis of a capsule exterior of the body-insertable apparatus.

21. The in-vivo image acquiring method according to claim 20, wherein the partial-image data is acquired by inputting an outside light from a part of an inner periphery region of the imaging target to the imaging unit of the body-insertable apparatus through an imaging window of an exterior case, the imaging window being formed between both ends of the exterior case along the longitudinal direction.

22. The in-vivo image acquiring method according to claim 21, wherein the partial-image data is acquired by inputting an outside light from a part of an inner periphery region of the imaging target to the imaging unit of the body-insertable apparatus, the imaging target corresponding to a field of vision defined by the imaging window.

23. The in-vivo image acquiring method according to claim 19, wherein at least acceleration data on a movement of the body-insertable apparatus is acquired as the position related data.

24. The in-vivo image acquiring method according to claim 19, further comprising:
detecting an acceleration of the body-insertable apparatus, by an acceleration sensor unit, wherein
the partial image data is acquired at plural times according to a detected result of the acceleration sensor unit.

25. The in-vivo image acquiring method according to claim 19, wherein an acquisition of the partial image data is not performed in a period in which a moving direction of the body-insertable apparatus becomes opposite.

* * * * *